United States Patent [19]

Horiba et al.

[11] 4,236,827
[45] Dec. 2, 1980

[54] OPTO-ACOUSTIC GAS ANALYZER

[75] Inventors: Atushi Horiba; Osamu Saitoh; Kozo Ishida, all of Miyanohigashi, Japan

[73] Assignee: Horiba, Ltd., Kyoto, Japan

[21] Appl. No.: 966,052

[22] Filed: Dec. 4, 1978

[51] Int. Cl.$^3$ ............................................. G01N 21/34
[52] U.S. Cl. ................................... 356/437; 250/343; 250/351
[58] Field of Search ................ 356/437, 432; 250/343, 250/351

[56] References Cited

U.S. PATENT DOCUMENTS

| | | | |
|---|---|---|---|
| 3,723,731 | 3/1973 | Blau | 250/343 |
| 3,820,901 | 6/1974 | Kreuzer | 250/345 |
| 3,947,685 | 3/1976 | Meinel | 250/343 |
| 4,055,764 | 10/1977 | Dimeff | 250/343 |

FOREIGN PATENT DOCUMENTS

| | | | |
|---|---|---|---|
| 1123139 | 2/1962 | Fed. Rep. of Germany | 250/343 |
| 1240307 | 5/1967 | Fed. Rep. of Germany | 250/343 |

OTHER PUBLICATIONS

Delany, M. E., "The Opto-Acoustic Effect in Gases," *Science Progress*, vol. XLVII, No. 187, Jul. 1959, pp. 459–467.

*Primary Examiner*—John K. Corbin
*Assistant Examiner*—R. A. Rosenberger
*Attorney, Agent, or Firm*—Wenderoth, Lind & Ponack

[57] ABSTRACT

An opto-acoustic gas analyzer has a black body light source, a chopper in the path of the light emitted from the light source for intermittently intercepting the light from the light source, a positive interference filter in the path of the light for filtering out light other than the wavelengths of light absorbed by the gas being analyzed, and an opto-acoustic detector which receives the filtered light and through which the gas to be analyzed is passed. A pressure change detector provided is provided in the opto-acoustic detector for detecting pressure changes in the gas and producing an electric signal corresponding such changes.

1 Claim, 7 Drawing Figures

OPTO-ACOUSTIC GAS ANALYZER

The present invention relates to an opto-acoustic gas analyzer which uses a light source composed of a black body and further utilizes an opto-acoustic detector. The opto-acoustic gas analyzer of the invention can be made at low cost, and is constructed so as to make it possible to analyze qualitatively and quantitatively for small amounts of gaseous components contained in atmospheric air, such as carbon monoxide gas, and to carry out such analysis stably and accurately.

In an opto-acoustic gas analyzer of the prior art, a laser ray is used as the energy source. However, this makes the analyzer too expensive and moreover, makes the analyzer large, not compact.

The main object of the present invention is to provide an opto-acoustic gas analyzer which can be manufactured in a compact form and at a low cost, yet which has superior stability. This object is achieved by using a light source composed of a black body which emits light of a continuous spectra, such as nichrome wire, a silconite source, a tungsten lamp, etc., in place of the laser light source of the prior art, and at the same time, using an optical filter.

The invention will now be explained in more detail in connection with the accompanying drawings, in which.

Figure 1:
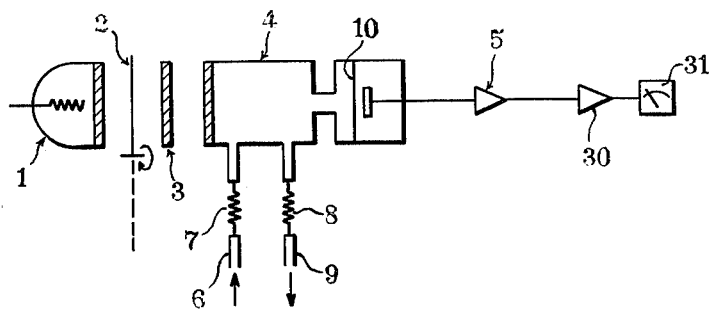
FIG. 1 is a schematic view of a first embodiment of the present invention.

FIG. 1 shows the first example of the opto-acoustic gas analyzer according to the present invention, and which is composed of a black body light source 1, a chopper 2, and a positive interference filter 3 consisting of a plurality of solid film layers which pass only a band of light having wavelengths in the region of light absorbed by the gaseous component for which analysis is to be carried out. The analyzer further has an opto-acoustic detector 4 with a microphone type condenser 10a with a diaphragm 10, and a means for detecting pressure changes in the gas within the detector and producing an electric signal corresponding to those changes. In FIG. 1, this means is a microphone type condenser 10a and a diaphragm 10, and a high impedance amplifier 5 connected to the condenser. Infrared ray energy emitted from the black body light source 1 is first intercepted intermittently by the chopper 2 and then filtered while passing through the positive filter 3. Thus, only the infrared rays having wavelengths in the region in which lie wavelengths of light absorbed by the gaseous component to be measured fall on the detector 4. A sample gas is continuously or intermittently introduced into the detector 4 from an inlet 6 through a capillary 7 and is exhausted through a capillary 8 and an outlet 9 after being circulated through the inside of the detector 4. If a gaseous component which will absorb light having wavelengths in the range of wavelengths of the infrared light is contained in the sample gas, this gaseous compound absorbs infrared energy. As a result, the pressure within the detector 4 increases. If the chopper 2 is operating so as to intercept the infrared rays intermittently at a proper frequency, the diaphragm 10 of the condenser 10a will be displaced at a frequency corresponding to the rotational speed of the chopper and, of course, the periodical displacement of the diaphragm can be taken out of the condenser 10a as a signal indicating the pressure of the gaseous component. It is not necessary that the pressure change detecting means be a microphone type as shown in FIG. 1. For example, a mass-flow type, which detects gas flow occurring within the detector by a hot-wire anemometer, will do as well. The absorption of infrared ray energy within the detector 4 is proportional to the concentration of the gaseous component to be measured, and therefore it is also possible to carry out a quantitative analysis for the gaseous component contained in the sample gas. Using the amplifier 5, the change of microphone capacity of the condenser 10a caused by movement of the diaphragm 10 is taken out as an electric signal which is rectified by a rectifier 30 and then used to move the needle of an indicator means 31.

Figure 2:
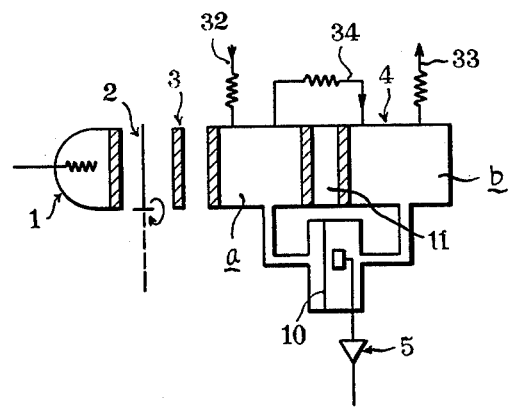
FIG. 2 is a schematic view of a second embodiment of the invention.
Figure 4:
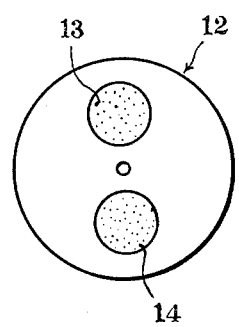
FIG. 4 is a sectional view of a gas filter and is taken along line IV—IV in FIG. 3.

FIG. 2 shows a second embodiment of the gas analyzer of the present invention, which is designed to function in a superior manner to the first embodiment. In the apparatus of the first embodiment, it is difficult to remove satisfactorily the interference effect which is caused by the presence in the gas being analyzed of a second or an interfering component and which is produced when the band of wavelengths of infrared rays absorbed by the interfering component is situated very near the frequency band of infrared rays absorbed by the gaseous component for which analysis is being carried out, or when the concentration of the component for which analysis is being carried out is very low compared with the concentration of the interfering component. In order to overcome this difficulty, in the second embodiment, the structure of the light-receiving chamber of the detector 4 is changed to a differential type, that is, as shown in FIG. 4, the detector 4 has two light-receiving compartments a and b. Means is provided to detect the pressure difference between the compartments which is due to the difference in energy absorption in the two compartments. A gas containing filter 11 is provided between the two compartments. This can be replaced by a solid filter. A gas inlet 32, a gas outlet 33 and a gas connection 34 are provided for compartments a and b.

For example, where a small concentration of carbon monoxide is present in atmospheric air along with carbon dioxide, which is an interfering component, and it is desired to measure the quantity of carbon monoxide, the second embodiment of the gas analyzer of the present invention can be used. The infrared ray light emitted from the black body light source 1 is first intercepted intermittently by a chopper 2, for example being chopped into intermittent light with a frequency of 10 Hz. It then passes through the interference filter 3 having a plurality of solid film layers and reaches the detector 4. If both compartments a and b are filled with a gas which does not absorb the infrared rays, upon the arrival of the infrared rays at the detector, there will be no pressure increase in either compartment and no displacement of the condenser diaphragm 10 occurs, since no energy absorption of the infrared rays occurs in either compartment. However, if atmospheric air containing carbon dioxide gas and a small quantity of carbon monoxide is enclosed in both compartments a and b, energy absorption will occur in both compartments and a displacement of the condenser diaphragm 10 proportional to the concentration of the carbon monoxide occurs, as will be described in detail, and thus, the concentration of carbon monoxide is accurately quantitatively determined without being distorted by the presence of the carbon dioxide.

It should be pointed out that the energy of the infrared rays which enter the compartment a has an energy distribution within a definite wave length region of the infrared spectra as determined by the interference filter 3, the center of which region is about $4.6\mu$. The infrared absorption band of carbon dioxide gas is situated very near to the infrared absorption band of carbon monoxide gas and those two absorption bands partially overlap each other. This overlapping, of course, occurs within the energy range of the wavelengths of infrared light rays passed through the filter 3. Therefore, the infrared rays arriving in the compartment a are absorbed by the small quantity of carbon monoxide gas, the quantity of energy given up to those gases being proportional to the initial intensity of the infrared rays. In other words, the temperature in compartment a increases. If the energy absorption in the compartment a is designated $\Delta I_a$, the absorption is in the following relation:

$$\Delta I_a = \Delta I_{CO} + \Delta I_{CO_2},$$

wherein $\Delta I_{CO}$ is the energy absorbed by the CO in the compartment a and $\Delta I_{CO_2}$ is the energy absorbed by the $CO_2$ in the compartment a. Since the amount of absorbed energy $\Delta I_a$ is small, the infrared rays, the energy intensity of which is almost equal to that of the infrared rays initially reaching the compartment a, enters the gas containing filter 11. In the filter 11, the same gas as the gas for which the analysis is being carried out (in the present case, carbon monoxide) is enclosed in an appropriate concentration. During passage through the filter 11, the intensity of the infrared rays in the region of the main absorption band of carbon monoxide is reduced and infrared energy consisting mainly of side bands of said main absorption band of CO, i.e. side bands of the band of infrared rays passed through the filter 3, passes through the filter 11 and enters the compartment b. Here again, in compartment b, the absorption of the infrared spectra due to the presence of carbon monoxide and carbon dioxide occurs in amounts corresponding to the concentrations thereof and the temperature in the compartment b increases. The energy $\Delta I_b$ absorbed by the gases in compartment b is:

$$\Delta I_b = \Delta I_{CO}' + \Delta I_{CO_2}',$$

wherein $\Delta I_{CO_2}'$ is the energy absorbed by the CO in compartment b and $\Delta I_{CO_2}'$ is the energy absorbed by the $CO_2$ in compartment b. By providing a solid filter 3 having an appropriate value of the half band width and a gas filter 11 having carbon monoxide gas in a proper concentration, semi-empirically, it is possible to obtain the following relation:

$$\Delta I_{CO_2} = \Delta I_{CO_2}'.$$

The difference in energy absorption in the two compartments or, in other words, the difference in the increase in pressure in the two compartments produces a displacement of the condenser diaphragm 10. The energy difference $\Delta E$ is:

$$\Delta E = \Delta I_a - \Delta I_b$$
$$= \Delta I_{CO} + \Delta I_{CO_2} - (\Delta I_{CO}' + \Delta I_{CO_2}')$$

Since $$\Delta I_{CO_2} = \Delta I_{CO_2}',$$

$$\Delta E = \Delta I_{CO} - \Delta I_{CO}'.$$

Since $\Delta I_{CO}'$ is the energy absorbed by the CO gas in the compartment b from the infrared rays which have lost considerable energy in the main absorption band of CO gas while passing through the filter 11, this energy is much smaller than $\Delta I_{CO}$; that is:

$$\Delta I_{CO} >> \Delta I_{CO}'.$$

Moreover, since $\Delta I_{CO}$ and $\Delta I_{CO}'$ are proportional to the concentration of CO gas in the gas being analyzed, $\Delta E$ is also proportional to the concentration of CO gas in the gas being analyzed. Thus, a signal corresponding to the amount of CO gas present and undisturbed by the presence of $CO_2$ gas is produced. This signal can be electrically amplified by amplifier 5 and displayed in an appropriate manner.

Thus, by making the detector a differential detector by providing a pair of light-receiving compartments in series and at the same time providing a gas filter containing a gas or solid which absorbs light in the same infrared spectra as that of the gas for which the analysis is being made, it is possible to provide a gas analyzer having a high accuracy in the quantitative analysis for the gas present only in a small quantity and at a low cost.

Figure 3:
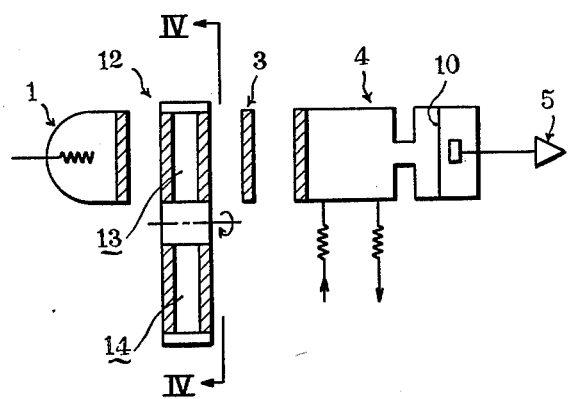
FIG. 3 is a schematic view of a third embodiment.

FIG. 3 shows the third embodiment of the present invention. The third embodiment achieves the same effect as the second embodiment by the use of a rotational gas filter 12 in combination with a detector 4 as provided in FIG. 1.

Figure 5:
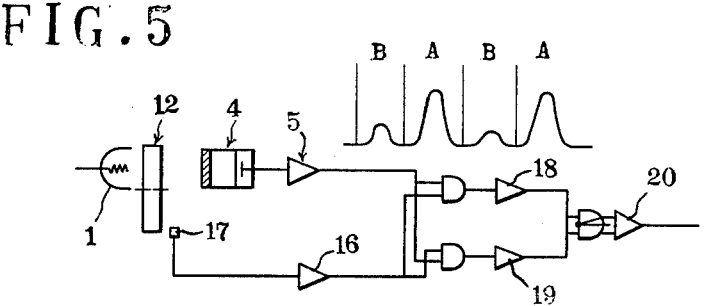
FIG. 5 is a schematic view for explaining the operation of the apparatus shown in FIG. 3; and, FIG. 6 is a view similar to FIG. 4 showing an example of a gas analyzer which is useful for the quantitative analysis of multiple gaseous components.

The third embodiment of the present invention will be described in detail in connection with the analysis of atmospheric air having carbon dioxide co-existing with a small quantity of carbon monoxide. Infrared rays emitted from a black body light source 1, after passing through the rotational gas filter 12, pass through an interference filter 3 consisting of a plurality of solid film layers and reach the detector 4. In one cell 13 of the rotational gas filter 12 is a gas which does not absorb the energy of the infrared rays and in the other cell 14 is the same gas as the gas for which the analysis is being carried out (in the specific example, carbon monoxide) and in an appropriate concentration. The infrared rays passing through the filter cell 13 are absorbed by the CO and $CO_2$ molecules in the opto-acoustic detector 4 and the temperature in the chamber of the detector increases. Thus, a displacement of the condenser diaphragm 10 occurs as explained in connection with the first embodiment. The signal produced at the condenser 10a from this displacement can be designated signal A. On the other hand, the infrared rays passing through the filter cell 14 have had absorbed therefrom the energy in the wavelength region corresponding to the main absorption band for CO gas, and when these rays arrive at detector 4, the absorption of infrared rays is mainly due to the existence of $CO_2$ gas in the detector 4. This also causes a signal to appear. This signal can be denoted as signal B. As shown in FIG. 5, the signals A and B are generated alternately at a frequency determined by the speed of rotation of the rotational filter 12. They are amplified by a pre-amplifier 5 and are sent to corresponding hold-amplifiers 18 and 19 as inputs thereto by the application of a synchronous signal generated from a synchronous signal generator 17 and amplified by amplifier 16. Finally, a final signal output (B−A) can be obtained by a subtracter 20. Thus, an output corresponding to the concentration of carbon monoxide gas can be supplied to an indicator, which output is unaffected by the presence of an interfering gas.

Figure 6:
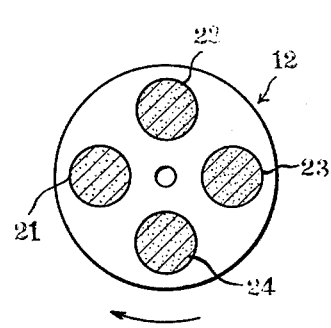

Furthermore, it is also possible to construct a gas analyzer which can be used for the quantitative analysis of a plurality of gaseous components, by providing a rotational filter 12 having a plurality of gas cells, each provided with an interference filter consisting of a plurality of film layers for the window of the cell, the number of cells being twice the number of gaseous components for which the analysis is to be made. FIG. 6 shows an example of such a rotational filter having four gas cells 21-24, wherein the cell 21 is filled with CO gas, the cell 22 is filled with $N_2$ gas, a gas which does not absorb infrared rays, the cell chamber 23 is filled with $CO_2$ gas and the cell 24 is filled with $N_2$ gas, and wherein an interference filter having a plurality of film layers for filtering out the wavelengths other than those absorbed by the CO gas is used as the window of the cells 21 and 22 and an interference filter having multiple film layers for filtering out the wavelengths other than those absorbed by the $CO_2$ gas is used as the window of the cells 23 and 24.

The concentration of CO gas is measured by the combination of the cell 21 and cell 22. The concentration of $CO_2$ gas is measured by the combination of the cell 23 and cell 24.

Figure 7:
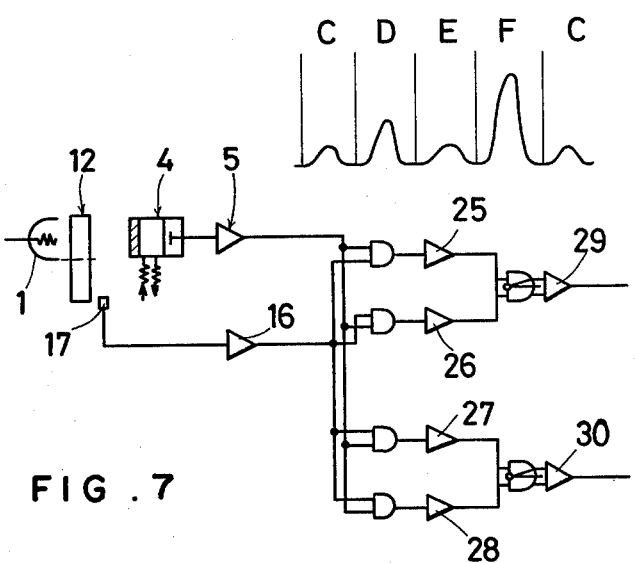
FIG. 7 is a schematic view for explaining the operation of the apparatus which has a rotational filter 12 as shown in FIG. 6.

FIG. 7 is a schematic view for explaining the operation of the apparatus which has a rotational filter 12 shown in FIG. 6. In FIG. 7, output signals taken out from the detector corresponding to the cells 21, 22, 23 and 24 are indicated as C, D, E and F respectively. At a frequency determined by the speed of rotation of the rotational filter 12, signals C, D, E and F are generated from the pre-amplifier 5 in that order. Signals C, D, E and F are sent to corresponding hold-amplifiers 25, 26, 27 and 28 as inputs thereto by the application of a syncronous signal generated from a syncronous signal generator 17 and amplified by amplifier 16.

Finally, a final signal output (C−D) can be obtained by a subtracter 29 and a final signal output (E−F) can be obtained by a subtracter 30.

As described above in detail, since the apparatus of the present invention uses a black body light source and a positive interference filter having a plurality of film layers, it is a stable gas analyzer which can be built at a low cost. The invention provides a gas analyzer which does not have a zero drift from the theoretical standpoint on its construction.

What is claimed is:

1. An opto-acoustic gas analyzer comprising a black body light source, a chopper means in the path of the light emitted from said light source for intermittently intercepting the light from said light source, a separate positive interference filter in the path of the light from said chopper and having a plurality of film layers for filtering from the light wavelengths of light other than the wavelengths of light absorbed by the gas for which analysis is being conducted, and an opto-acoustic detector for receiving the filtered light from said positive interference filter and having two compartments therein which are aligned in the direction of the passage therethrough of light from said light source, a filter means between said two compartments for filtering from the light passing therethrough at least some of the light having wavelengths in the range of wavelengths absorbed by the gas for which the analysis is being conducted, means for passing the gas to be analyzed into one of said compartments and from said one compartment to the other compartment and out of the other compartment, and a separate chamber connected to said two compartments and said detector further having pressure change detecting means in said separate chamber and producing an electric signal corresponding to such changes.

* * * * *